US010493243B1

(12) United States Patent
Braham

(10) Patent No.: US 10,493,243 B1
(45) Date of Patent: Dec. 3, 2019

(54) RESPIRATORY AIRWAY AND INTRAVENOUS EXTENSION SYSTEM (RAIVES)

(71) Applicant: Antonio Braham, Sacramento, CA (US)

(72) Inventor: Antonio Braham, Sacramento, CA (US)

( * ) Notice: Subject to any disclaimer, the term of this patent is extended or adjusted under 35 U.S.C. 154(b) by 0 days.

(21) Appl. No.: 16/033,957

(22) Filed: Jul. 12, 2018

Related U.S. Application Data

(63) Continuation of application No. 15/960,038, filed on Apr. 23, 2018.

(51) Int. Cl.
| | | |
|---|---|---|
| *A61M 25/02* | (2006.01) | |
| *F16B 2/10* | (2006.01) | |
| *A61M 16/08* | (2006.01) | |

(52) U.S. Cl.
CPC ............ *A61M 25/02* (2013.01); *A61M 16/08* (2013.01); *F16B 2/10* (2013.01); *A61M 2025/024* (2013.01); *A61M 2209/082* (2013.01)

(58) Field of Classification Search
USPC ................ 248/72, 63, 68.1, 74.4, 83, 49, 55
See application file for complete search history.

(56) References Cited

U.S. PATENT DOCUMENTS

| | | | | | |
|---|---|---|---|---|---|
| 1,032,436 | A | * | 7/1912 | Smith | B43K 23/001 24/11 CT |
| 2,667,678 | A | * | 2/1954 | Hargrave | B42F 1/006 24/508 |
| 3,111,296 | A | * | 11/1963 | Ludes | A61J 9/0638 24/507 |
| RE29,037 | E | * | 11/1976 | Caveney | H01B 13/01209 269/131 |
| 4,707,906 | A | * | 11/1987 | Posey | A61G 7/0503 128/DIG. 26 |
| 4,722,120 | A | * | 2/1988 | Lu | B42F 1/10 24/489 |
| 4,887,784 | A | * | 12/1989 | Kayali | B60N 3/102 248/311.2 |
| 5,135,189 | A | * | 8/1992 | Ghazizadeh | F16M 11/40 248/104 |
| 5,640,742 | A | * | 6/1997 | White | A44C 3/001 24/18 |

(Continued)

OTHER PUBLICATIONS

JannaBand; One Hospital Bed—One Call Button—One JanaBand;; [retrieved on Feb. 5, 2019]; retrieved from the Internet: http://www.janaband.net 1 page.

(Continued)

*Primary Examiner* — Monica E Millner
(74) *Attorney, Agent, or Firm* — Fish & Richardson P.C.

(57) ABSTRACT

An apparatus has a first side plate and a second side plate. A spring is configured to engage with the first side plate and the second side plate, where the spring provides a spring bias to each of the first side plate and to the second side plate to bias a lower portion of the first side plate and a lower portion of the second side plate together into a default closed position. A medical extension device channel is configured into each of the first side plate and the second side plate. Two anchor points are configured as part of each of the first side plate and the second side plate.

18 Claims, 12 Drawing Sheets

(56) References Cited

U.S. PATENT DOCUMENTS

| | | | | |
|---|---|---|---|---|
| 5,666,702 A * | 9/1997 | Ming-Chieh | ............ | B42F 1/006 24/338 |
| 6,804,866 B2 * | 10/2004 | Lemke | ............... | A61M 16/0683 24/3.11 |
| 6,925,689 B2 * | 8/2005 | Folkmar | ................... | F16B 2/10 24/30.5 R |
| 7,210,658 B2 * | 5/2007 | Carrera | ................. | F16L 3/1218 248/58 |
| 7,217,031 B2 * | 5/2007 | Bhavnani | ........... | G04B 37/1413 24/3.12 |
| 7,559,125 B2 * | 7/2009 | Cofer | .................. | A61M 5/1418 24/487 |
| 7,766,313 B2 * | 8/2010 | Panosian | ................. | B25B 5/003 269/3 |
| 7,850,329 B2 * | 12/2010 | Henry | ....................... | F21L 4/04 362/191 |
| 7,918,828 B2 * | 4/2011 | Lundgaard | .......... | A61M 5/1418 248/229.1 |
| 8,020,825 B2 * | 9/2011 | Dostaler | ............ | A47G 23/0225 24/332 |
| 8,073,518 B2 * | 12/2011 | Chin | ................... | A61B 5/14552 600/310 |
| 9,657,893 B2 * | 5/2017 | Buresh, II | ............ | F16M 13/022 |
| 9,717,888 B2 * | 8/2017 | Sos | ........................ | A61M 25/09 |
| 9,999,719 B2 * | 6/2018 | Kitchen | ............... | A61M 5/1415 |
| 2004/0118982 A1 * | 6/2004 | Shillings | .................. | F16L 3/223 248/68.1 |
| 2006/0021203 A1 * | 2/2006 | Nails | ........................ | A44B 9/18 24/499 |
| 2009/0019678 A1 * | 1/2009 | Taylor | .................. | A61M 5/1418 24/530 |
| 2011/0192951 A1 * | 8/2011 | Gooch | .................... | F16M 11/12 248/316.7 |
| 2013/0068914 A1 * | 3/2013 | MacGillivray | ......... | B60R 11/06 248/523 |
| 2013/0097822 A1 * | 4/2013 | Mayberry | ................. | F16B 2/10 24/509 |
| 2014/0007408 A1 * | 1/2014 | Nool | ....................... | B65D 25/22 29/525.01 |
| 2018/0087714 A1 * | 3/2018 | Goffman | .............. | F16M 13/022 |
| 2018/0200485 A1 * | 7/2018 | Braham | ................ | A61M 25/02 |

OTHER PUBLICATIONS

MarketLab; Unique & Hard-to-Find Laboratory and Medical Supplies; "IV Line Holder"; [retrieved on Feb. 5, 2019]; retrieved from the Internet: https://www.marketlab.com/iv-line-holder/p/IVLineHolder/ 1 page.

Da Vinci Medical, Inc.; "IV Line, Medical Tube Holder & Organizer"; [retrieved from the internet on Feb. 5, 2019]; retrieved from the internet: https://www.youtube.com/watch?v=IMofUqH2CTg ; 1 page.

NewMediaWire; "Introducing the Perfect Gift for Nurses on Certified Nurses Day: The Easy View IV Tube Separator!"; [retrieved from the internet on Feb. 5, 2019]; retrieved from the internet: https://app.newmediawire.com/news/531ddac2875a520007b3afd1/introducing-the-perfect-gift-for-nurses-on-certified-nurses-day-the-easy-view-iv-tube-separator ; 4 pages.

The Beata Clasp; [retrieved from the internet on Feb. 5, 2019]; http://www.beataclasp.com/ ; 2 pages.

Research Gate; "Edwards Vamp System"; [retrieved from the internet on Feb. 5, 2019]; retrieved from the internet: htips://www.research.gate.net/figure/Edwards-VAMP-system-The-port-to-the-right-of-the-image-is-the-sampling-port-which-is_fig1_236956639 ; 4 pages.

Tucker Hemphill; "IV-Buddy"; [retrieved from the internet on Feb. 5, 2019]; retrieved from: https://www.tuckerhemphill.com/iv-buddy/ ; 19 pages.

Vitality Medical.com; Dale Hold-N-Place Foley Catheter Holder; [retrieved from the internet on Feb. 5, 2019]; retrieved from the internet: https://www.vitalitymedical.com/dale-foley-catheter-holder.html ; 9 pages.

* cited by examiner

RESPIRATORY AIRWAY AND INTRAVENOUS EXTENSION SYSTEM (RAIVES)

CROSS REFERENCE TO RELATED APPLICATION

This application is a continuation of U.S. patent application Ser. No. 15/960,038, filed on Apr. 23, 2018, which is hereby incorporated by reference in its entirety.

BACKGROUND

Patients in medical facilities are typically attached to various types of monitoring and medically assistive equipment (for example, intravenous (IV) and respiratory devices). Attachment to the medically assistive equipment is accomplished using various medical extension devices (MEDs) (for example, IV and respiratory tubing, lead wires, and cables). Transferring a patient (for example, from a gurney to a bed or vice versa) or re-positioning the patient (for example, rotating the patient from a supine to a lateral position) while attached to the medically assistive equipment can be cumbersome due to the attached MEDs.

SUMMARY

The present disclosure describes a respiratory airway and intravenous (IV) extension system (RAIVES).

In an implementation, an apparatus has a first side plate and a second side plate. A spring is configured to engage with the first side plate and the second side plate, where the spring provides a spring bias to each of the first side plate and to the second side plate to bias a lower portion of the first side plate and a lower portion of the second side plate together into a default closed position. A medical extension device channel is configured into each of the first side plate and the second side plate. Two anchor points are configured as part of each of the first side plate and the second side plate.

Some particular implementations of the described subject matter, including the previously described implementation, can be implemented in a configuration using a computer-implemented method; a non-transitory, computer-readable medium storing computer-readable instructions to perform the computer-implemented method; and a computer-implemented system comprising one or more computer memory devices interoperably coupled with one or more computers and having tangible, non-transitory, machine-readable media storing instructions that, when executed by the one or more computers, perform the computer-implemented method/the computer-readable instructions stored on the non-transitory, computer-readable medium.

The subject matter described in this disclosure can be implemented in particular implementations so as to realize one or more of the following advantages. First, the described RAIVES permits MEDs (for example, IV and respiratory tubing, lead wires, and cables) to be easily transferred from one patient treatment platform (for example, a gurney or hospital bed) attachment point to another (for example, moved from a gurney rail to a hospital bed rail (or vice versa) or from one hospital bed rail to another hospital bed rail. Second, the RAIVES can keep MEDs organized and grouped for easy identification and maintenance. In some medical facilities (for example, on Telemetry floors or in emergency departments (such as, intensive care units (ICUs) or emergency rooms (ERs))), it is important that MEDs are kept neatly in proximity to each other and off the medical facility floor where they could be stepped on, tripped over, or contaminated by dirt or organisms tracked in on footwear. Third, use of the RAIVES with MEDs can eliminate medical waste when using medical tape, tongue depressors, and other valuable medical resources to created improvised MED organization solutions. Fourth, the RAIVES can be configured with sensors or to interface with other sensors that can be used to alert medical personnel if a patient is attempting to extricate himself or herself from a patient treatment platform. Medical personnel can use the RAIVES (for example, as part of a medical monitoring system) to help secure the patient to a patient treatment platform and to prevent/mitigate, for example, falls and damage to medical equipment. Fifth, the described RAIVES implementations can be configured as a completely disposable medical resource to avoid additional costs to enable re-use (such as, sterilization). This can be especially important in situations dealing with hazardous infectious organisms where patient and healthcare provider safety is paramount after medical equipment comes into contact with blood and other bodily fluids. In some implementations, some portions of the RAIVES can be configured of materials that can be sterilized (for example, stainless steel or aluminum) to permit disassembly, cleaning, sterilization in an autoclave/disinfecting chemical, and reassembly. In a general use scenario, portions of the RAIVES can be replaceable with new, sterile components configured as desired. Sixth, in some implementations, the RAIVES can be configured of recyclable, biodegradable, or environmentally friendly materials to protect the environment. Other advantages will be apparent to those of ordinary skill in the art.

The details of one or more implementations of the subject matter of this specification are set forth in the Detailed Description, the Claims, and the accompanying drawings. Other features, aspects, and advantages of the subject matter will become apparent to those of ordinary skill in the art from the Detailed Description, the Claims, and the accompanying drawings.

DESCRIPTION OF DRAWINGS

Like reference numbers and designations in the various drawings indicate like elements.

DETAILED DESCRIPTION

The following detailed description describes a respiratory airway and intravenous (IV) extension system (RAIVES) apparatus and use, and is presented to enable any person skilled in the art to make and use the disclosed subject matter in the context of one or more particular implementations. Various modifications, alterations, and permutations of the disclosed implementations can be made and will be readily apparent to those of ordinary skill in the art, and the general principles defined can be applied to other implementations and applications, without departing from the scope of the present disclosure. In some instances, one or more technical details that are unnecessary to obtain an understanding of the described subject matter and that are within the skill of one of ordinary skill in the art may be omitted so as to not obscure one or more described implementations. The present disclosure is not intended to be limited to the described or illustrated implementations, but to be accorded the widest scope consistent with the described principles and features.

Patients in medical facilities are typically attached to various types of monitoring and medically assistive equipment (for example, IV and respiratory devices). Attachment to the medically assistive equipment is accomplished using various medical extension devices (MEDs) (for example, IV and respiratory tubing, lead wires, and cables). Transferring a patient (for example, from a gurney to a bed or vice versa) or re-positioning the patient (for example, rotating the patient from a supine to a lateral position) while attached to the medically assistive equipment can be cumbersome due to the attached MEDs.

At a high-level, the RAIVES is an apparatus that is mountable on medical equipment, particularly rails of patient treatment platforms, such as gurneys and hospital beds. The RAIVES permits MEDs to be organized and managed between a medical assistive device and a patient on a patient treatment platform. The RAIVES also allows MEDs attached to a patient to be easily moved/reorganized on a particular patient treatment platform or moved from one patient treatment platform to another patient treatment platform (for example, when moving a patient to/from an ICU or ER, to a different hospital room, or from an ambulance gurney to an ICU or ER).

Figure 1:
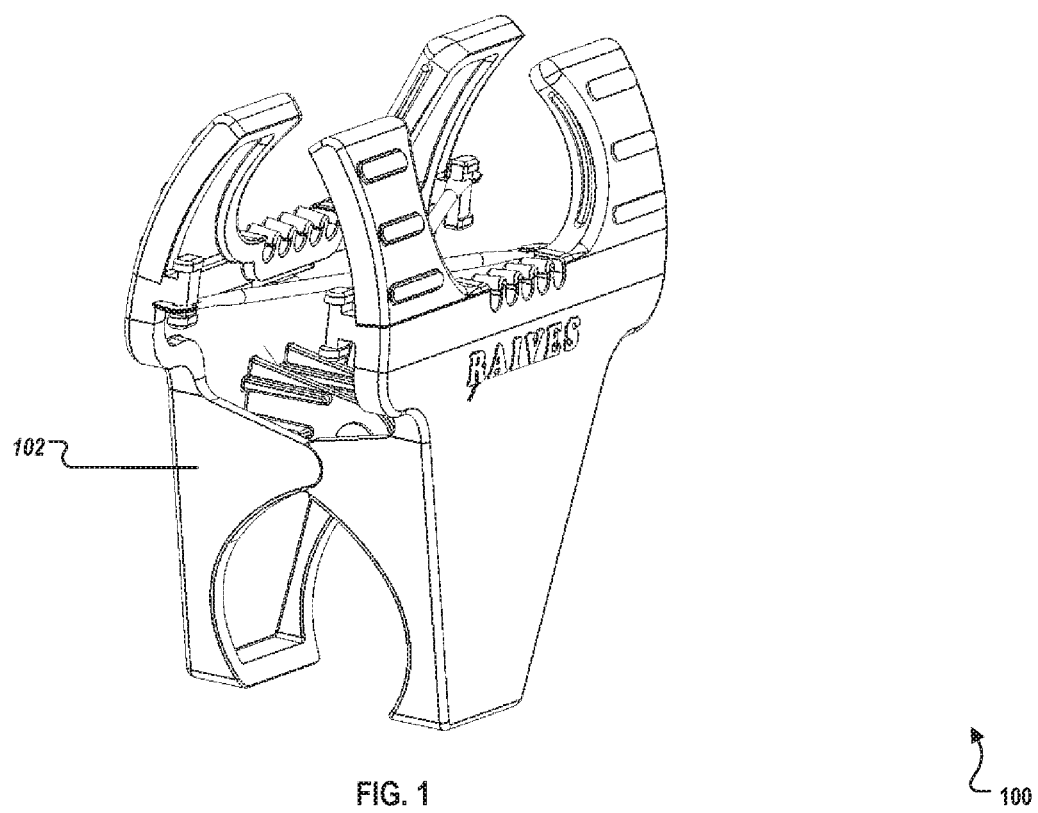
FIG. 1 is a perspective view of a respiratory airway IV Extension System (RAIVES), according to an implementation of the present disclosure.

Turning now to FIG. 1, FIG. 1 is a perspective view 100 of a RAIVES 102, according to an implementation of the present disclosure. The illustrated RAIVES 102 is a clip-type apparatus that can be used to permit MEDs (for example, IV and respiratory tubing, lead wires, and cables) to be easily transferred from one patient treatment platform (for example, a gurney or hospital bed) attachment point to another (for example, moved from a gurney rail to a hospital bed rail (or vice versa) or from one hospital bed rail to another hospital bed rail. As illustrated, implementations of the described side plates are configured with pinch tabs (for example, refer to elements 402*a* and 402*b* in FIG. 4A) to permit the pinch tabs to be pinched together to open the RAIVES 102 or to be released to close the RAIVES 102.

The RAIVES 102 can keep MEDs organized and grouped for easy identification and maintenance. In some medical facilities (for example, on Telemetry floors or in emergency departments (such as, intensive care units (ICUs) or emergency rooms (ERs))), it is important that MEDs are kept neatly in proximity to each other and off the medical facility floor where they could be stepped on, tripped over, or contaminated by dirt or organisms tracked in on footwear.

The RAIVES 102 can eliminate medical waste when using medical tape, tongue depressors, and other valuable medical resources to created improvised MED organization solutions. Some RAIVES 102 implementations can be configured as a completely disposable medical resource to avoid additional costs to enable re-use (such as sterilization). This can be especially important in situations dealing with hazardous infectious organisms where patient and healthcare provider safety is paramount after medical equipment comes into contact with blood and other bodily fluids.

In some implementations, some components of the RAIVES 102 can be configured of materials that can be sterilized (for example, stainless steel or aluminum) to permit disassembly, cleaning, sterilization in an autoclave/disinfecting chemical, and reassembly. In a general use scenario, particular portions of the RAIVES 102 can be configured to be replaceable with new, sterile components (for example, described securing bands), as desired. In some implementations, the RAIVES 102 can be configured of recyclable, biodegradable, or environmentally friendly materials to protect the environment. Other advantages will be apparent to those of ordinary skill in the art.

Figure 2:
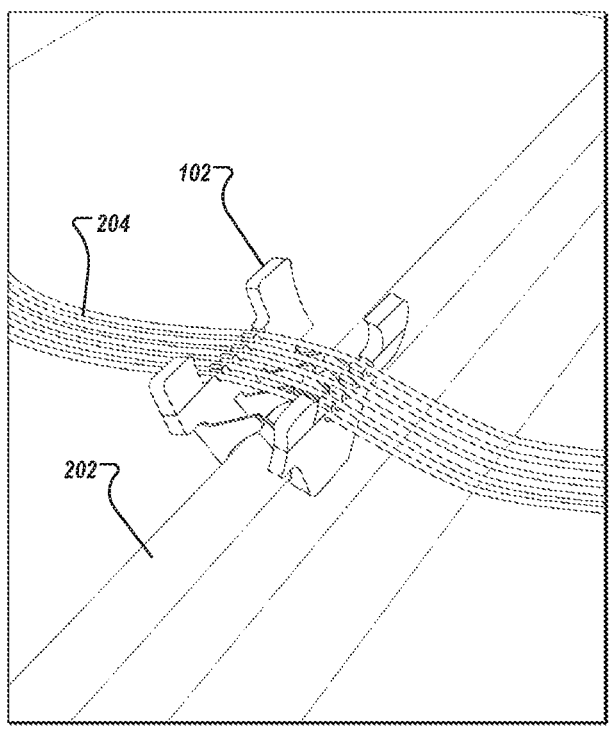
FIG. 2 is perspective view of the RAIVES of FIG. 1, mounted to a patient treatment platform, according to an implementation of the present disclosure.
Figure 2:

FIG. 2 is perspective view 200 of the RAIVES 102 of FIG. 1, mounted to a patient treatment platform, according to an implementation of the present disclosure. As illustrated, the RAIVES 102 is attached to an example rail 202 of a hospital-bed-type patient treatment platform. The RAIVES 102 is configured to clip securely to the circumference of the example rail 202. Some implementations of the RAIVES 102 can be configured in varying sizes to permit secure attachment to differing sizes of rails 202 or other patient treatment platform structures (for example, an IV bag stand, lamp stand, or other vertical standing tubular structure). In some implementations, the RAIVES 102 can be directly clipped to patient treatment platform linens or patient clothing.

MEDs 204 (here illustrated as a group of various IV tubes, lead wires, and cables) are disposed across the top of the RAIVES 102 and between the pinch tabs of each side plate of the illustrated RAIVES 102. The MEDs 204 are secured to the RAIVES 102 with one or more securing bands (for example, refer to elements 310*a* and 310*b* in FIG. 3A).

Figure 3A:
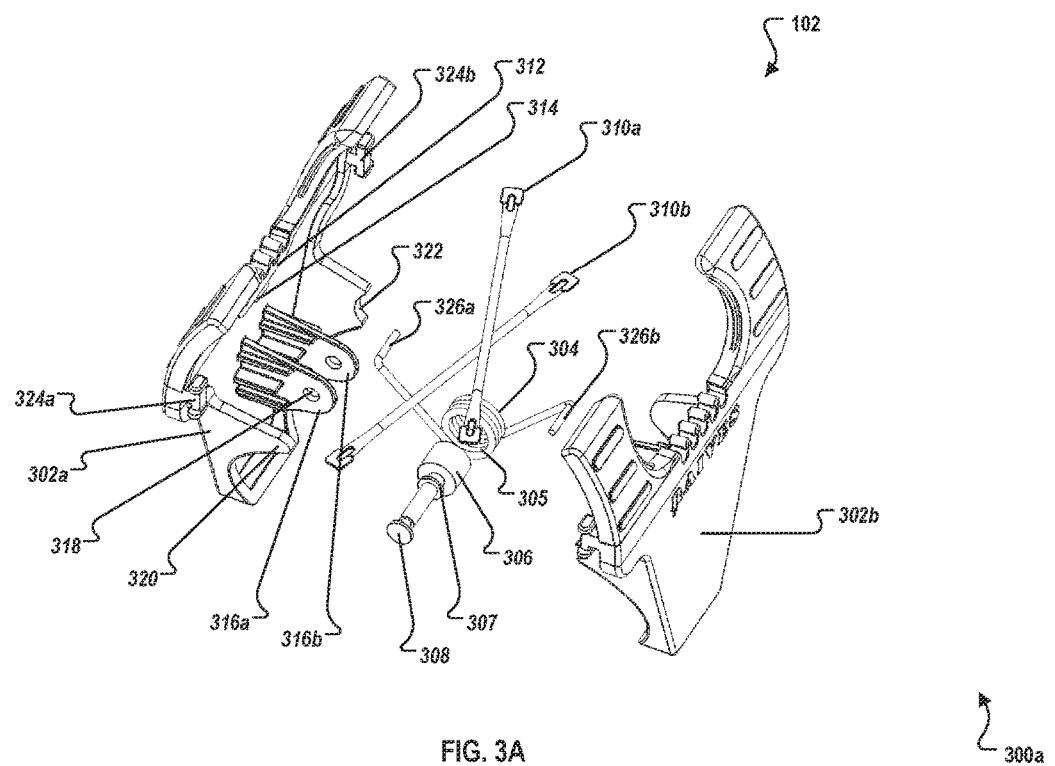
FIG. 3A is an exploded top perspective view of the RAIVES of FIG. 1, according to an implementation of the present disclosure.

FIG. 3A is an exploded top perspective view 300*a* of the RAIVES 102 of FIG. 1, according to an implementation of the present disclosure. In some implementations, the illustrated RAIVES 102 includes two side plates 302*a*/302*b*, spring 304, pivot cylinder 306, locking rivet 308, and securing bands 310*a* and 310*b*.

Each of the side plates 302*a*/302*b* are configured to define a spring tail engagement slot 312, a spring tail support shelf 314 (also refer to FIGS. 3B and 4A for alternative views), two pivot arms 316*a*/316*b*, male pivot point 320, female pivot point 322, and securing band anchor points 324*a*/324*b*.

In various implementations, side plates 302a/302b can be configured of metal, polymers, composites, or other materials.

In the illustrated implementation, spring 304 is a wire-type coiled spring configured to define a central coil 305 and a ninety-degree-angled spring tail 326a/326b on each end of the spring 304. The central coil 305 is configured with an interior diameter substantially similar to the outer diameter of pivot cylinder 306. The central coil 305 is also configured to be of a length to hold pivot cylinder 306 within the interior of central coil 305. Pivot cylinder 306 is configured to be of a diameter and length to fit within the central coil 305. Spring 304 is also configured with a ninety-degree-angled spring tail 326a/326b on each end of the spring 304. Spring 304 can be configured of metal, polymers, composites, or other materials. Spring 304 provides a spring bias with both an outward and a downward component with respect to the interior and top, respectively, of each side plate 302a/302b. The RAIVES 102 is configured so that the spring bias provided by spring 304 biases the RAIVES 102 into a default closed position when spring tails 326a/326b are moved closer together around the longitudinal axis of the central coil 305. The spring bias provides mechanical force necessary to "clip" the RAIVES 102 to patient treatment platforms or other structures using the bottom of side plates 302a/302b.

Pivot cylinder 306 is configured to define a cylindrical channel 307 along the long axis of the pivot cylinder 306, and with an interior diameter substantially similar to the outer diameter of locking rivet 308. Locking rivet 308 is configured to fit within the cylindrical channel 307 of the pivot cylinder 306. Pivot cylinder 306 can be configured of metal, polymers, composites, or other materials.

As illustrated, locking rivet 308 is a two-piece, double-cap-type rivet with a cap at each end of locking rivet 308. In some implementations, locking rivet 308 can be configured to be a friction/push-type lock, screw-type lock, or other type of locking mechanism. Locking rivet 308 can be configured of metal, polymers, composites, or other materials.

Pivot arms 316a/316b are configured to extend outward from the interior of each side plate 302a/302b. Pivot arms 316a/316b are configured to be separated by an interior distance substantially similar to the configured length of the central coil 305/pivot cylinder 306 plus the width of both pivot arms 316a/316b of the matching side plate. Each pivot arm 316a/316b also defines a circular opening 318 to receive the locking rivet 308. The circular opening 318 is configured with an interior diameter substantially similar to the outer diameter of the locking rivet 308.

Each side plate 302a/302b defines a male pivot point 320 and a female pivot point 322. In the illustrated implementation, the male pivot point 320 is configured to define a convex, semi-circular surface to engage with the female pivot point 322. The female pivot point 322 is configured to define a concave semi-circular surface to engage with the male pivot point 322. Note that each side plate is configured identically, but when oriented where the interior of the side plates 302a/302b face each other, the male pivot point 320 and a female pivot point 322 mechanically couple to form a pivot point on each side of the RAIVES 102.

To assemble the RAIVES 102, the following description can be instructive. Pivot cylinder 306 is inserted into central coil 305 of spring 304. Spring tail 326a of spring 304 is inserted into the spring tail engagement slot 312 of side plate 302a, where the spring tail 326a is proximate to, and rests against, an upper surface of the spring tail support shelf 314 of side plate 302a. Similarly, spring tail 326b of spring 304 is inserted into the spring tail engagement slot 312 of side plate 302b, where the spring tail 326b is proximate to, and rests against, an upper surface of the spring tail support shelf 314 of side plate 302b. Side plates 302a/302b are moved proximate to each other. Central coil 305 of spring 304 is placed between pivot arms 316a/316b of side plate 302a, and pivot arms 316a/316b of corresponding side plate 302b are placed in a relationship with pivot arms 316a/316b of side plate 302a and central coil 305. For example (such as, shown in FIGS. 5 and 6), pivot arm 316a (side plate 302a), pivot arm 316b (side plate 302b), central coil 305, pivot arm 316b (side plate 302a), and pivot arm 316a (side plate 302b). As will be apparent to those of ordinary skill in the art, other configurations of these components are also possible. At this point, the male pivot point 320 and female pivot point 322 of side plate 302a is engaged with a corresponding female pivot point 322 and male pivot point 320, respectively, of side plate 302b.

Locking rivet 308 is separated, and a first piece is inserted into circular opening 318 from the outer surface of a first pivot arm of a set of two pivot arms, through the two pivot arms (for example, pivot arm 316a (side plate 302a) and pivot arm 316b (side plate 302b)), through cylindrical channel 307 of pivot cylinder 306/central coil 305, and toward a second set two pivot arms (for example, pivot arms 316b (side plate 302a) and pivot arm 316a (side plate 302b)). The second piece of locking rivet 308 is pushed through a circular opening 318 from the outer surface of a first pivot arm of the second set of two pivot arms to mechanically couple to, and engage with, the first piece of the locking rivet 308. The heads of each piece of locking rivet 308 are configured of a diameter larger than the interior diameter of holes 318. The coupled locking rivet 308 maintains the RAIVES 102 in an assembled state. To disassemble the RAIVES 102, locking rivet 308 can be separated and each piece removed from the RAIVES 102 to allow the described components to separate.

Once assembled, one or more securing bands 310a/310b can be attached to the RAIVES 102 using securing band anchor points 324a/324b on each side of side plate 302a/302b. Securing bands 310a/310b are typically configured with an elastic loop on each end, which permits the end of the securing band to stretch over a securing band anchor point 324a/324b. Once the end of the securing band 310a/310b is attached to a securing band anchor point (for example, 324a), the securing band 310a/310b is stretched to attach the opposite end of the securing band 310a/310b to another securing band anchor point (for example, 324b). To prevent the securing bands 310a/310b from being lost from the securing band anchor points 324a/324b, one or both ends of a securing band 310a/310b can be configured to attach to a securing band anchor point 324a/324b using, for example, screws, clamps, hooks, or male/female interlocking structures.

Figure 4A:
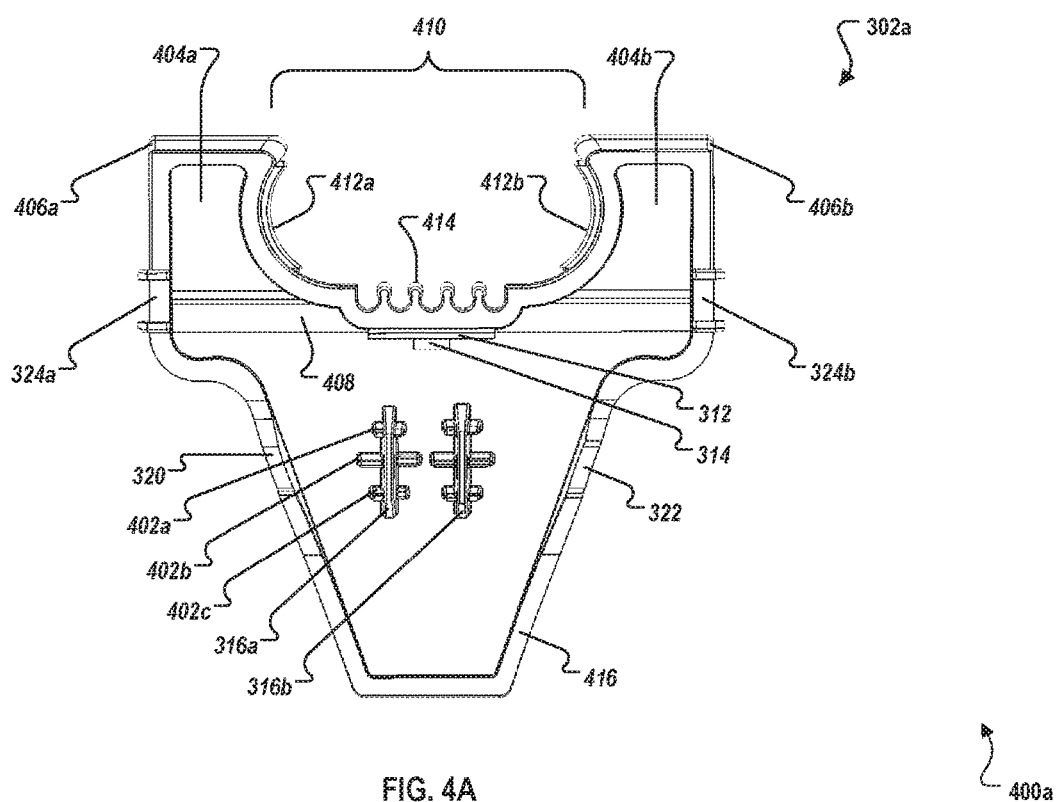
FIG. 4A is an interior view of a side plate of FIGS. 3A and 3B, according to an implementation of the present disclosure.

The elastic tension generated by the stretched and secured securing band is used to secure MEDs to the RAIVES 102 against guidance elements (refer to element 414 in FIG. 4A). In some implementations, the securing bands can be configured to form an 'X'-type pattern by attaching each end of securing band to opposite securing band anchor points on each side plate. For example, securing band anchor point 324a (side plate 302a)/securing band anchor point 324a (side plate 302b) and securing band anchor point 324b (side plate 302a)/securing band anchor point 324b (side plate 302b). Other securing band configurations are also possible. For example, each end of a securing band can be attached to both securing band anchor points on each side plate. In some implementations, ends of two or more securing bands can be attached to a single securing band anchor point to provide additional holding force for MEDs (for example, MEDs 204 of FIG. 2). In other implementations, both ends of a securing band can be attached to the same securing band anchor point to form a loop to hold MEDs. For example, MEDs could be attached to one or more sides of a RAIVES 102 within the loop formed by one or more securing bands.

In some implementations, the RAIVES 102 can be configured to support a cover (not illustrated) that is attached (for example, with some type of adhesive) to the inner surface of each side plate 302a/302b and positioned over the spring 304 and other internal components of the RAIVES 102. In some implementations, the cover can be an elastomeric-type sheet or cloth. The cover can be used to ensure that one or more MEDs are not damaged (for example, abraded, crimped, or pinched) by contact with the spring 304 or other internal components of the RAIVES 102.

Figure 3B:
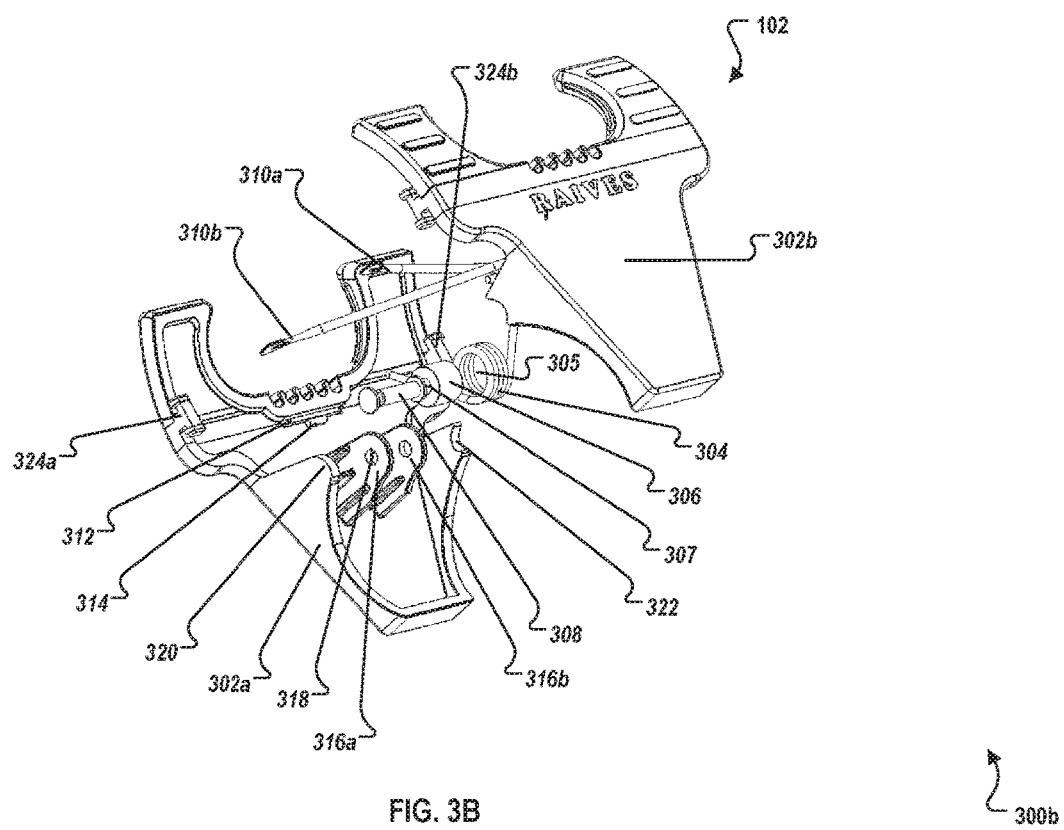
FIG. 3B is an exploded bottom perspective view of the RAIVES of FIG. 1, according to an implementation of the present disclosure.

FIG. 3B is an exploded bottom perspective view 300b of the RAIVES 102 of FIG. 1, according to an implementation of the present disclosure. FIG. 3B better illustrates the spring tail engagement slot 312 and the spring tail support shelf 314 described in FIG. 3A. Also better illustrated are internal components and surfaces of the side plate 302a.

FIG. 4A is an interior view 400a of a side plate 302a of FIGS. 3A and 3B, according to an implementation of the present disclosure. As illustrated, in FIG. 4A, the side plate 302a includes support ribs 402a, 402b, and 402c on each side of each pivot arm 316a/316b. The support ribs 402a/402b/402c form a three-point concave pivot point for the end of the corresponding opposite side plate 302b pivot arm 316b to engage with. For example, refer to FIG. 4B, where it can be seen that the ends of support ribs 402a and 402c extend further along the longitudinal axis of each pivot arm 316a/316b than support rib 402b. The support ribs form a pocket-type pivot point for opposite pairs of pivot arms to bear against when the RAIVES 102 is assembled, as previously described.

Side plate 302a also includes pinch tabs 404a/404b and pinch surfaces 406a/406b. Pinch tabs 404a/404b provide engagement surfaces for fingers of healthcare professionals to permit the upper surfaces of side plates 302a/302b to be pinched together. The act of pinching the upper surfaces of side plates 302a/302b together moves spring tails 326a/326b closer together and causes compression of the central coil 305 of spring 304. The increased spring bias causes the side plates 302a/302b to pivot around the longitudinal axis of the locking rivet 308 to separate the pinch tabs 404a/404b of the side plates 302a/302b when a healthcare professional releases the pinch tabs 404a/404b on each side of the RAIVES 102.

In some implementations, each outer surface of pinch tabs 404a/404b can be configured to be covered with the pinch surfaces 406a/406b. In some implementations, pinch surfaces 406a/406b can be configured of an elastomeric-type material (rubber, plastic, latex, nitrile, or silicon) adhered to the outer surface of the pinch tabs 404a/404b or integrally-configured as part of the outer surface of the pinch tabs 404a/404b (for example, as a spiked-, grooved-, stippled-, or dimpled-type surface to increase finger adherence to each pinch tab 404a/404b. Pinch surfaces 406a/406b are configured to avoid damage (for example, by puncturing or tearing) to, and to protect the integrity of, protective clothing (such as, rubber or latex gloves) and MEDs proximate to the pinch surfaces 406a/406b. In some implementations, the pinch surfaces 406a/406b can be configured to be perma- nently adhered (for example, with a strong adhesive or heat) or to be removed and replaced on the side plate 302a. For example, the pinch surfaces 406a/406b can be configured to snap/friction fit onto the pinch tabs 404a/404b (for example, as a cover-type configuration or using a female-configured grooved structure or hole in the pinch tabs 404a/404b with a corresponding male-type protrusion from the inner portion of the pinch surfaces 406a/406b to engage with the pinch tabs 404a/404b). Other implementations can use a temporary adhesive, tape, or other adhering mechanism consistent with this disclosure to allow removal and replacement of the pinch surfaces 406a/406b.

Side plate 302a also includes a transverse strengthening ridge 408 that runs across the side plate 302a proximate to the base of the pinch tabs 404a/404b and aligned laterally with the interior of each of securing band anchor points 324a/324b. The strengthening ridge 408 provides support to the base of the pinch tabs 404a/404b to prevent cracking of the side plate 302a due to the force applied to the exterior surfaces of the pinch tabs 404a/404b when clamping the RAIVES 102 to a patient treatment platform or other object.

Side plate 302a is also configured to define a MED channel 410 to secure and guide various MEDs (for example, MEDs 204) as described. MED channel 410 can be configured with varying widths depending upon particular medical needs, types of MEDs, medical equipment and patient needs. For example, differing sizes of respiratory airway tubing can require a larger or smaller MED channel 410 for a secure fit, or securing bands can be used to help secure the respiratory airway tubing into a different sized (for example, larger) MED channel 410.

As illustrated, MED channel 410 also includes gripping surfaces 412a/412b for providing a friction-type fit for MEDs engaged with MED channel 410. For example, the outer surface of a respiratory airway tube can make contact with the gripping surfaces 412a/412b to help secure the respiratory airway tube within the MED channel 410. In some implementations, gripping surfaces 412a/412b can be configured of an elastomeric-type material (for example, rubber, plastic, latex, nitrile, or silicon) adhered to the inner surface of the walls of the MED channel 410 or integrally-configured as part of the inner surface of the walls of the MED channel 410 (for example, as a spiked-, grooved-, stippled-, or dimpled-type surface to increase surface roughness and friction between the gripping surfaces 412a/412b and one or more MEDs within MED channel 410. Gripping surfaces 412a/412b are configured to avoid damage to MEDs (for example, by puncturing or tearing) and to preserve the integrity of protective clothing (such as, rubber or latex gloves) that may come in contact with the gripping surfaces 412a/412b. In some implementations, the gripping surfaces 412a/412b can be configured to be permanently adhered (for example, with a strong adhesive or heat) or to be removed and replaced. For example, the gripping surfaces 412a/412b can be configured to snap/friction fit into the sides of the MED channel 410 (for example, into a female-configured grooved structure or hole in the walls of the MED 410 with a corresponding male-type protrusion from the wall-facing portion of the gripping surfaces 412a/412b to engage with the walls of the MED channel 410). Other implementations can use a temporary adhesive, tape, or other adhering mechanism consistent with this disclosure to allow removal and replacement of the gripping surfaces 412a/412b.

The MED channel 410 of each side plate 302a/302b is typically configured with a single row of raised guidance elements 414 used to secure MEDS (for example, IV tubing, lead wires, and cables) to the RAIVES 102 through the MED channel 410 (for example, as illustrated in FIG. 2) of both side plates 302a/302b. In other implementations, two or more rows of raised guidance elements 414 can be configured for use with each side plate 302a/302b. One or more securing bands 310a/310b can be used to further secure MEDs engaged with the raised guidance elements 414 to the RAIVES 102. For example, to permit secure organization and movement of IV tubes to a different location on a hospital bed rail (including a different hospital bed rail on the same hospital bed) or to a different patient treatment platform.

The raised guidance elements 414 are configured to secure a MED (for example, an IV tube) between each pair of raised guidance elements 414 to prevent lateral movement of the MED with respect to the row of raised guidance elements 414. In some implementations, each raised guidance element 414 is configured with a circular-shaped head and a circular-shaped trough between each pair of raised guidance elements 414 to secure a MED of a particular size (for example, an IV tube of a particular diameter) pushed down between each pair of raised guidance elements 414. In some alternative configurations, the raised guidance elements can be—configured to be conically shaped (for example, shaped similar to a cone, a blunted/truncated cone, or as bi-conic) or in a different shape consistent with this disclosure.

In some implementations, the raised guidance elements 414 can be configured to be a particular size or of differing sizes to fit various MED types within the RAIVES 102. In some implementations, the size (width and height), spacing, and number of the raised guidance elements 414 can be varied to support different MED sizes (for example, different diameter IV tubing). In some implementations, more than one MED can be stacked between each pair of raised guidance elements 414. In some implementations, one or more raised guidance elements 414 can be configured to contain a sensor element configured to be analyzed by a computer (see below for additional detail).

In some implementations, the raised guidance elements are configured of the same material as the corresponding side plate 302a/302b. In other implementations, the raised guidance elements can be configured of an elastomeric-type material that can compress, stretch, and bend (for example, rubber, plastic, latex, nitrile, or silicon) and adhered to the inner surface of the walls of the MED channel 410. The raised guidance elements 414 are configured to avoid damage (for example, by puncturing or tearing) MEDs and to preserve the integrity of protective clothing (such as, rubber or latex gloves) that may come in contact with the raised guidance elements 414.

In some implementations, the raised guidance elements 414 can be configured to be permanently adhered (for example, with a strong adhesive or heat) or to be removed and replaced (such as, to permit use with different types/sizes of MEDs). For example, the raised guidance elements 414 can be configured to snap/friction fit into the bottom of the MED channel 410 (for example, into a female-configured grooved structure or hole in the walls of the MED 410 with a corresponding male-type protrusion from the wall-facing portion of the raised guidance elements 414 to engage with the bottom of the MED channel 410). Other implementations can use a temporary adhesive, tape, or other adhering mechanism consistent with this disclosure to allow removal and replacement of the raised guidance elements 414.

Figure 6:
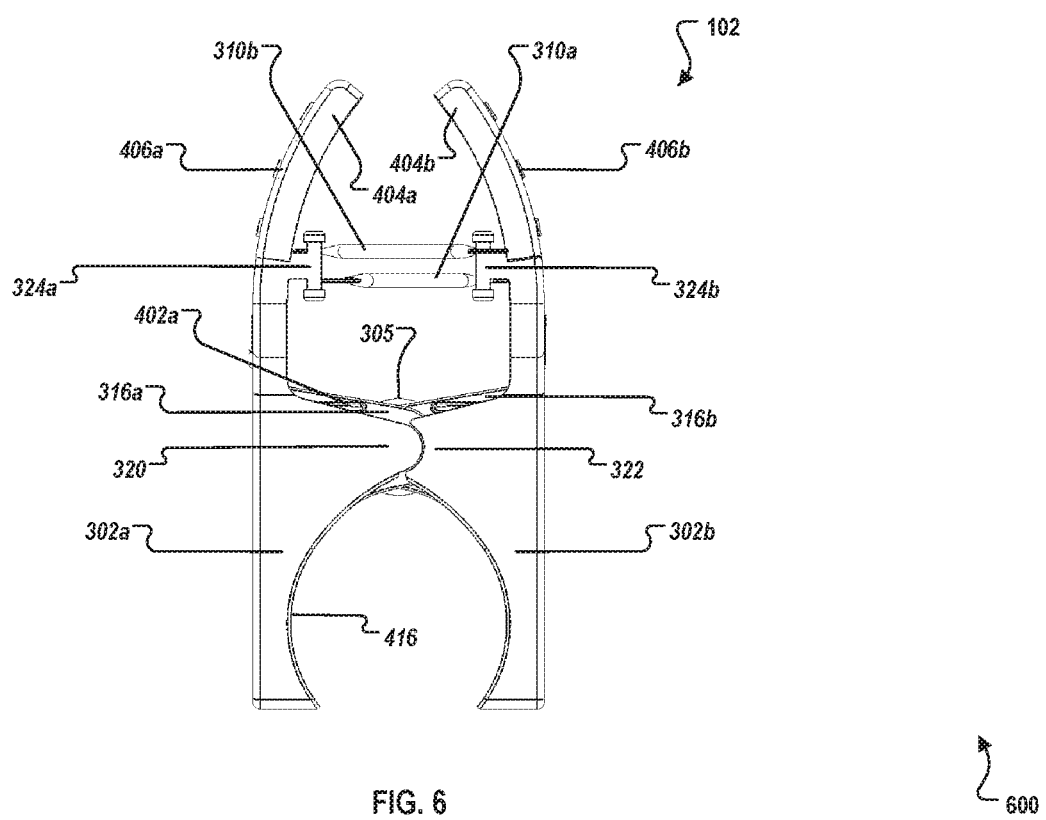
FIG. 6 is an end view of the RAIVES of FIG. 1, according to an implementation of the present disclosure.

Each side plate 302a/302b is also configured with a shaped (for example, semi-circular) clamping surface 416 to permit attachment of the RAIVES 102 to hospital bed rails, patient treatment platforms or other surfaces (such as, clothing or shelves). Refer to FIG. 6 for a view of the shaped clamping surfaces 416 of each side plate 302a/302b in opposition to each other in an assembled RAIVES 102.

Although not illustrated, in some implementations, clamping surface 416 can be configured to include an elastomeric-type gripping material (for example, rubber, plastic, latex, nitrile, or silicon) adhered to the inner surfaces of the clamping surface 416 or with a gripping surface integrally-configured as part of the inner surfaces of the walls of the clamping surface 416 (for example, as a spiked-, grooved-, stippled-, or dimpled-type surface to increase surface roughness and friction between the clamping surface 416 and an attachment surface. The clamping surface 416 is configured to avoid damage to attachment surfaces (for example, by puncturing, scratching or tearing) and to preserve the integrity of protective clothing (such as, rubber or latex gloves) that may come in contact with the clamping surface 416. In some implementations, the described gripping material of the clamping surface 416 can be configured to be permanently adhered (for example, with a strong adhesive or heat) or to be removed and replaced. For example, the gripping material can be configured to snap/friction fit into the clamping surface 416 (for example, into a female-configured grooved structure or hole with a corresponding male-type protrusion from the surface-facing portion of the gripping material to engage with the clamping surface 416). Other implementations can use a temporary adhesive, tape, or other adhering mechanism consistent with this disclosure to allow removal and replacement of the gripping material with respect to the clamping surface 416.

Figure 4B:
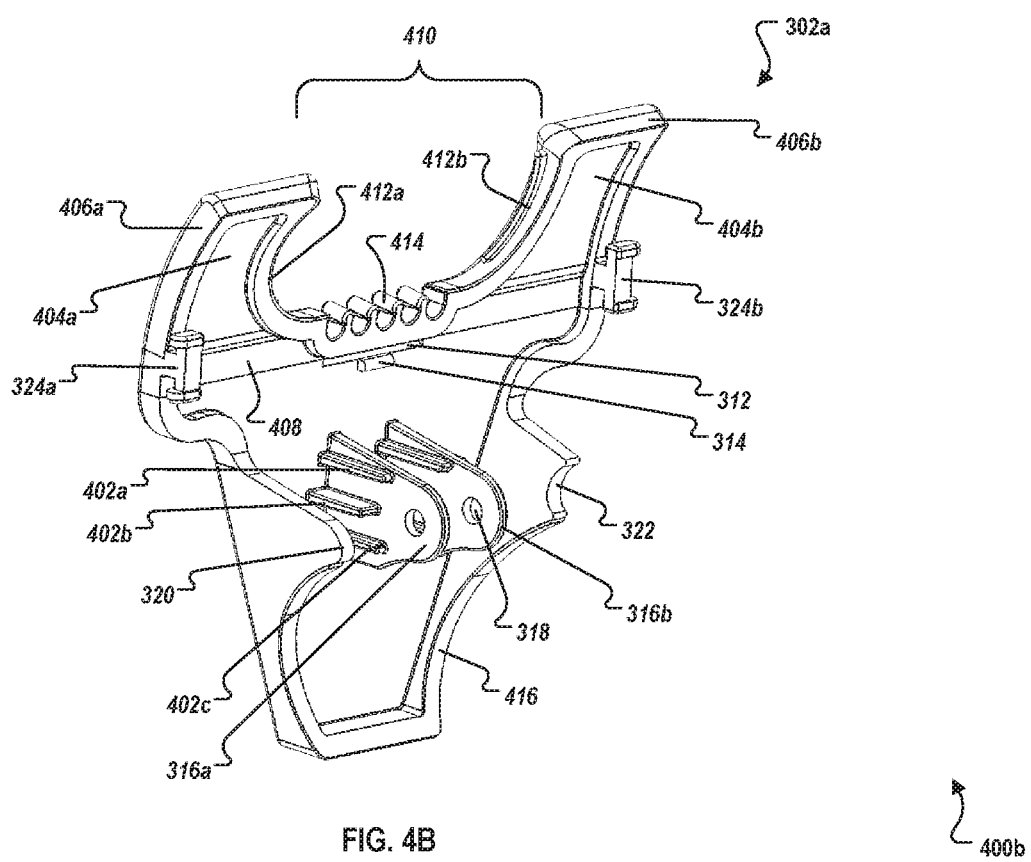
FIG. 4B is a perspective interior view of the side plate of FIG. 4A, according to an implementation of the present disclosure.

FIG. 4B is a perspective interior view 400b of the side plate 302a of FIG. 4A, according to an implementation of the present disclosure. As illustrated, FIG. 4B provides a clearer view of the size and shape of an implementation of anchor points 324a/324b. FIG. 4B also provides a perspective view of the pivot arms 316a/316b and configuration of the support ribs 402a, 402b, and 402c on each side of each pivot arm 316a/316b.

Figure 4C:
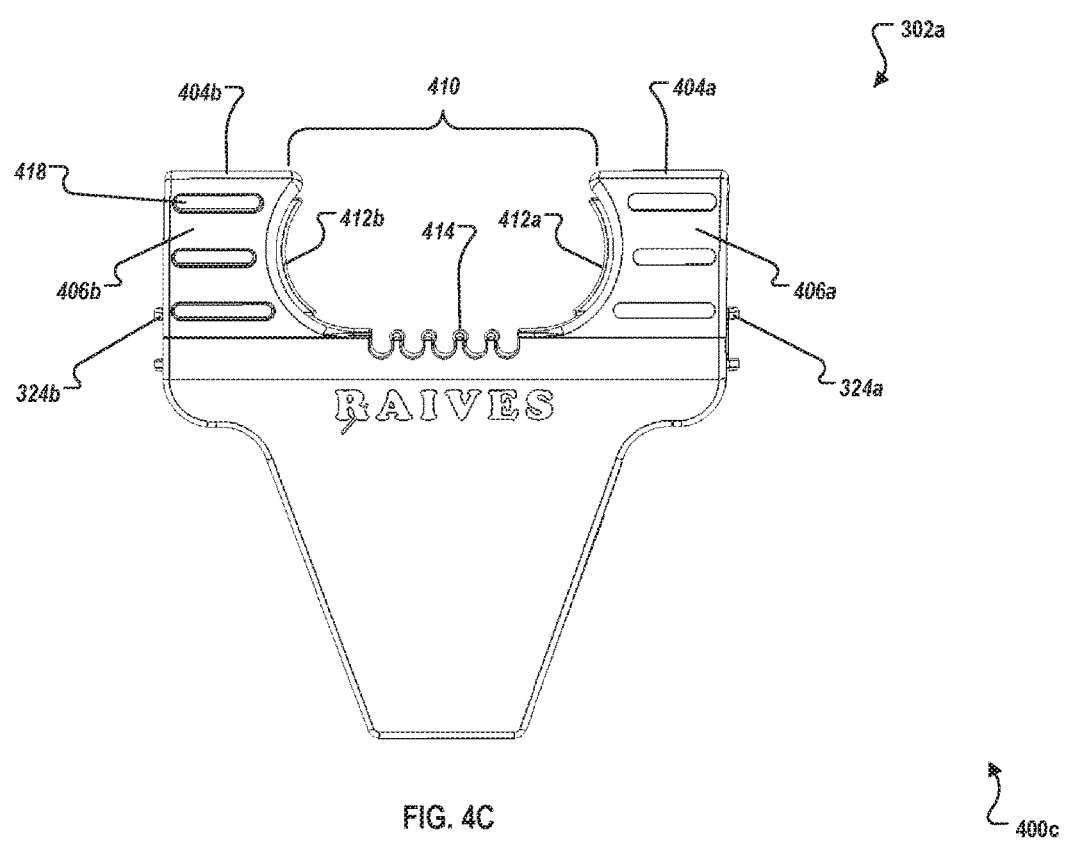
FIG. 4C is an exterior view of the side plate of FIGS. 4A and 4B, according to an implementation of the present disclosure.

FIG. 4C is an exterior view 400c of the side plate 302a of FIGS. 4A and 4B, according to an implementation of the present disclosure. Of note is that, in some implementations, some portions of anchor points 324a/324b extend beyond the sides of the side plates 302a/302b. Also, pinch surfaces 406a/406b are illustrated configured with ridges 418 to aid in operating the RAIVES 102.

Figure 5:
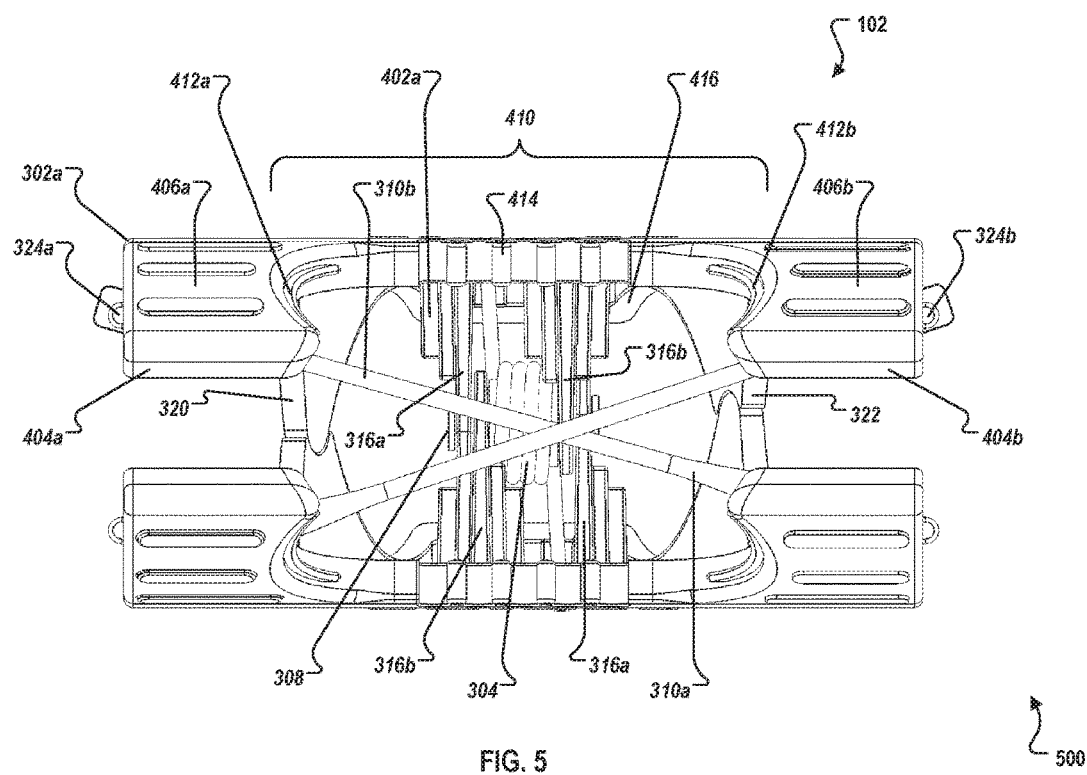
FIG. 5 is a top view of the RAIVES of FIG. 1, according to an implementation of the present disclosure.

FIG. 5 is a top view 500 of the RAIVES 102 of FIG. 1, according to an implementation of the present disclosure. FIG. 5 provides a spatial top view of the assembled components of the illustrated RAIVES 102. Of note is the illustrated relationship between the pivot arms 316a and 316a of each side plate 302a/302b and the engagement of corresponding male pivot points 320 and female pivot points 322. The spring bias provided by the spring tails 326a/326b on each end of the spring 304 biases the side plates 302a/302b to pivot around the longitudinal axis of the locking rivet 308 into a default closed configuration (touching) at the lower portions of the side plates 302a/302b.

FIG. 6 is an end view 600 of the RAIVES 102 of FIG. 1, according to an implementation of the present disclosure. FIG. 6 illustrates the RAIVES 102 in an open configuration as if the pinch tabs 404a/404b were being pinched together. Of note is the illustrated relationship between the pivot arms 316a and 316a of each side plate 302a/302b and the engagement of the illustrated corresponding male pivot point 320 and female pivot point 322. The spring bias provided by the spring tails 326a/326b on each end of the spring 304 (spring coil 305 shown) biases the side plates 302a/302b to pivot around the longitudinal axis of the locking rivet 308 (not illustrated) into a default closed configuration (touching) at the lower portions of the side plates 302a/302b.

Figure 7:
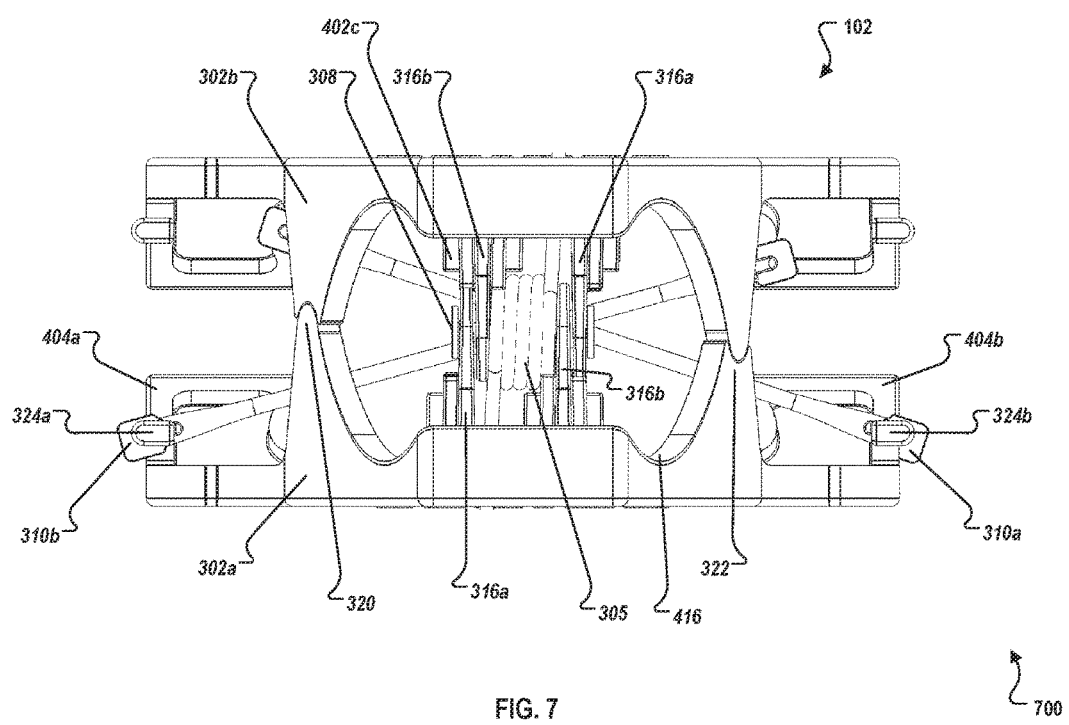
FIG. 7 is a bottom view of the RAIVES of FIGS. 1 and 6, according to an implementation of the present disclosure.

FIG. 7 is a bottom view 700 of the RAIVES 102 of FIGS. 1 and 6, according to an implementation of the present disclosure. In a manner similar to FIG. 5, FIG. 7 provides a spatial bottom view of the assembled components of the illustrated RAIVES 102. As in FIG. 6, FIG. 7 illustrates the RAIVES 102 in an open configuration as if the pinch tabs 404a/404b were being pinched together. Of note is the illustrated relationship between the pivot arms 316a and 316a of each side plate 302a/302b and the engagement of corresponding male pivot points 320 and female pivot points 322. Additionally, the attachment of one end of securing bands 310a/310b can be seen with respect to anchor points 324b/324a, respectively.

Figure 8:
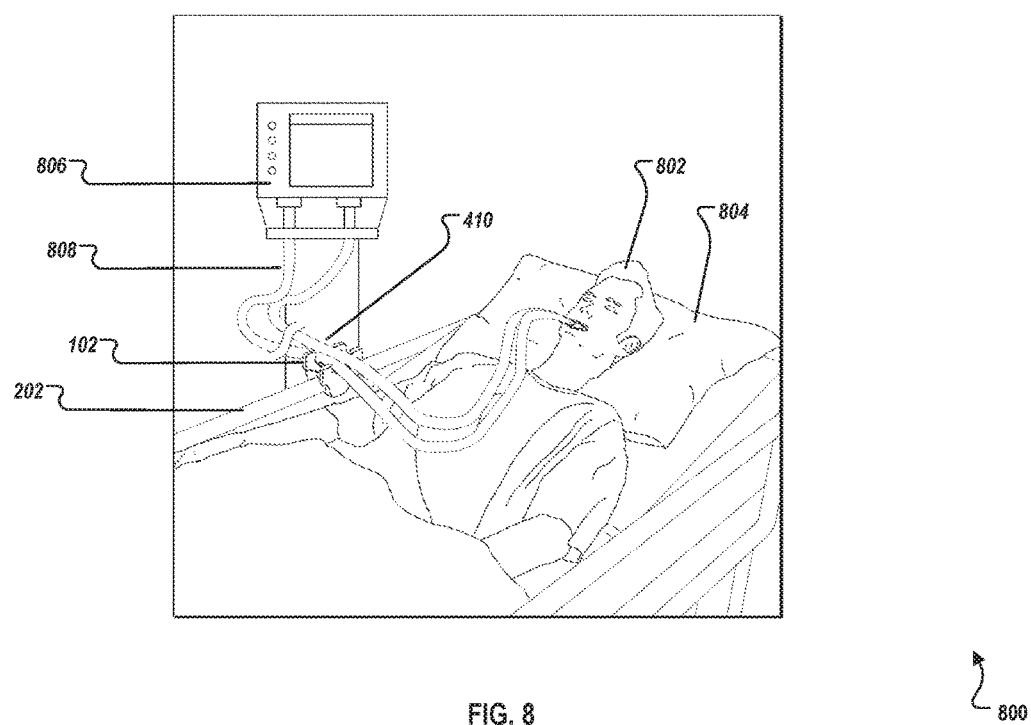
FIG. 8 is an illustration of a patient attached to a respiratory ventilation system using two RAIVES to secure respiratory airway tubes, according to an implementation of the present disclosure.

FIG. 8 is an illustration 800 of a patient attached to a respiratory ventilation system using a RAIVES to secure two respiratory airway tubes, according to an implementation of the present disclosure. In the illustration 800, a patient 802 (in a supine position) on a patient treatment platform 804 is attached to a mechanical ventilator 806 using MED 808 (here, two respiratory airway tubes). In typical implementations, a MED support (not illustrated) as separate free-standing support can be used to support the MED 808 between the patient 802 and the mechanical ventilator 806. The use of the RAIVES 102 permits easy placement of support for the MED 808 and for easy adjustment of MED 808 length between the mechanical ventilator 806 and the patient 802 (for example, if the patient is rotated into a lateral position).

As previously described, the RAIVES 102 defines a MED channel 410 to secure and guide various MEDs (here, two respiratory airway tubes 808 situated side-by-side in the MED channel 410). MED channel 410 can be configured with varying widths depending upon particular medical needs, types of MEDs, medical equipment and patient needs. For example, differing sizes of respiratory airway tubing can require a larger or smaller MED channel 410 for a secure fit, or securing bands can be used to help secure the respiratory airway tubing into a different sized (for example, larger) MED channel 410.

The following description provides an example use case of the RAIVES configuration illustrated in at least FIGS. 1-2, 3A-3B, 4A-4C, and 5-8. In some implementations, various described steps of the use case can be performed in a different order, consistent with this disclosure. Opening and engagement of the RAIVES with a structure (for example, a hospital bed rail) is analogous to the description above with respect to the RAIVES configuration described in at least FIGS. 1-2 and 8. Once secured to a desired structure, a respiratory-airway-type MED attached on one end to a mechanical ventilator (including associated humidification and other ventilation equipment) and to a patient on the other end can be pressed into the interior portion of a MED channel defined by the RAIVES. The MED channel engages the outer surface of the respiratory-airway-type MED to semi-secure the respiratory-airway-type MED at a particular position. If a patient needs, for example, to be rotated from a supine to a lateral position, a healthcare professional can grasp the respiratory-airway-type MED and, prior to, or while the patient is being rotated, pull the respiratory-airway-type MED through the MED channel to a desired position along the respiratory airway MED. To reduce slack, the respiratory airway MED can be pulled back in the opposite direction to increase the length of the respiratory-airway-type MED on the mechanical ventilator "side" of the RAIVES and to shorten the length of respiratory airway MED on the patient "side" of the RAIVES.

The following description provides another example use case of the RAIVES configuration illustrated in at least FIGS. 1-2, 3A-3B, 4A-4C, and 5-8. In some implementations, various described steps of the use case can, consistent with this disclosure, be performed in a different order. To open and engage the RAIVES with a structure (for example, a hospital bed rail), the RAIVES can be held in the hands by a human user and the pinch tabs on each of the side plates can be pressed together. As a particular example, a thumb from each hand can be placed on the pinch tabs of one side plate, an index finger from the corresponding hand can be placed on the opposite/corresponding pinch tab of the other side plate, and the thumb and index fingers brought together on each hand. Pressing the RAIVES side plates together will produce force to overcome the generated spring bias of a spring to cause male pivot points and female pivot points to bear against and rotate against each other and result in the lower portions of the side plates to open for engagement with a desired structure.

Once secured to a desired structure, MEDS (for example, IV tubes) can be run within the MED channel between the raised guidance elements which are perpendicular to the rotational axis of opening the RAIVES. Once the MEDS are in place, securing bands attached to each side plate are stretched over the MEDS and engaged with anchor points configured into each of the side plates to secure the MEDS between the raised guidance elements.

In some implementations, the described RAIVES configurations can include one or more sensors and computers (not illustrated). For example, a miniaturized computer system (for example, computer 902 below) can be attached to one or both RAIVES side plates (for example, side plates 302a/302b of FIG. 3A. The computer can include, among other things, various sensors (for example, auditory, infrared, magnetic, temperature, pressure, orientation, or flow), a battery, a timer, light-emitting elements (for example, small visual displays (such as, a liquid crystal display (LCD) or organic light-emitting diode (OLED)), light-emitting diodes (LEDs) or light bulbs), or audio emitting elements. In some implementations, the RAIVES can be configured with one or more wired/wireless data ports (for example, USB, FIREWIRE, WIFI, and BLUETOOTH). The data ports can be used to connect the RAIVES to other RAIVES, sensors, or computers.

As an example of use, a computer-equipped RAIVES could signal a specific orientation angle or position on a hospital bed rail, monitor that fluids are flowing through a particular IV tube, and monitor that electricity is flowing through a heart monitoring lead wire. In one example, the computer-equipped RAIVES could be networked into a hospital computer/medical monitoring system that can include other computer-equipped RAIVES or separate sensors to provide additional medical information to healthcare providers. Alarms (for example, visual, auditory, or network messages) could be generated to alert healthcare professionals if pre-programmed thresholds are met or exceeded. For example, if a patient tried to extricate themselves from a hospital bed, the RAIVES could generate one or more alarms based on a change in orientation of the RAIVES itself or a change in data values that are being monitored (for example, patient movement has disconnected the previously-described heart monitor lead wire and electricity is no longer being detected flowing through the heart monitor lead wire). In another example, a RAIVES that is interfaced with a medical monitoring computer/system, other sensors, or both can be used to alert medical personnel if triggered in some way. In this example, if a patient is attempting to extricate himself or herself from a patient treatment platform, a sensor (such as, a pressure pad) can generate an alert-type message to the medical monitoring computer to help the medical personnel secure the patient to the patient treatment platform.

In this manner, patient injuries (for example, through falls) can be prevented/mitigated to protect patient well-being and to avoid unnecessary equipment damage. In addition, preventing patients from exiting a patient treatment platform can help medical facilities to avoid potential legal liability due to patient injuries and to reduce overall costs due to any damaged equipment.

In some implementations, various components of the RAIVES can be configured with one or more of the above-described sensors to provide monitoring of one or more MEDS in proximity to the RAIVES. In some implementations, particular sensors can be attached to particular MEDS for individual monitoring purposes (for example, a sensor lead from the computer system can be attached to a respiratory tube to provide auditory monitoring of air flow through the respiratory tube). Other examples will be apparent to those of ordinary skill in the art.

Figure 9:
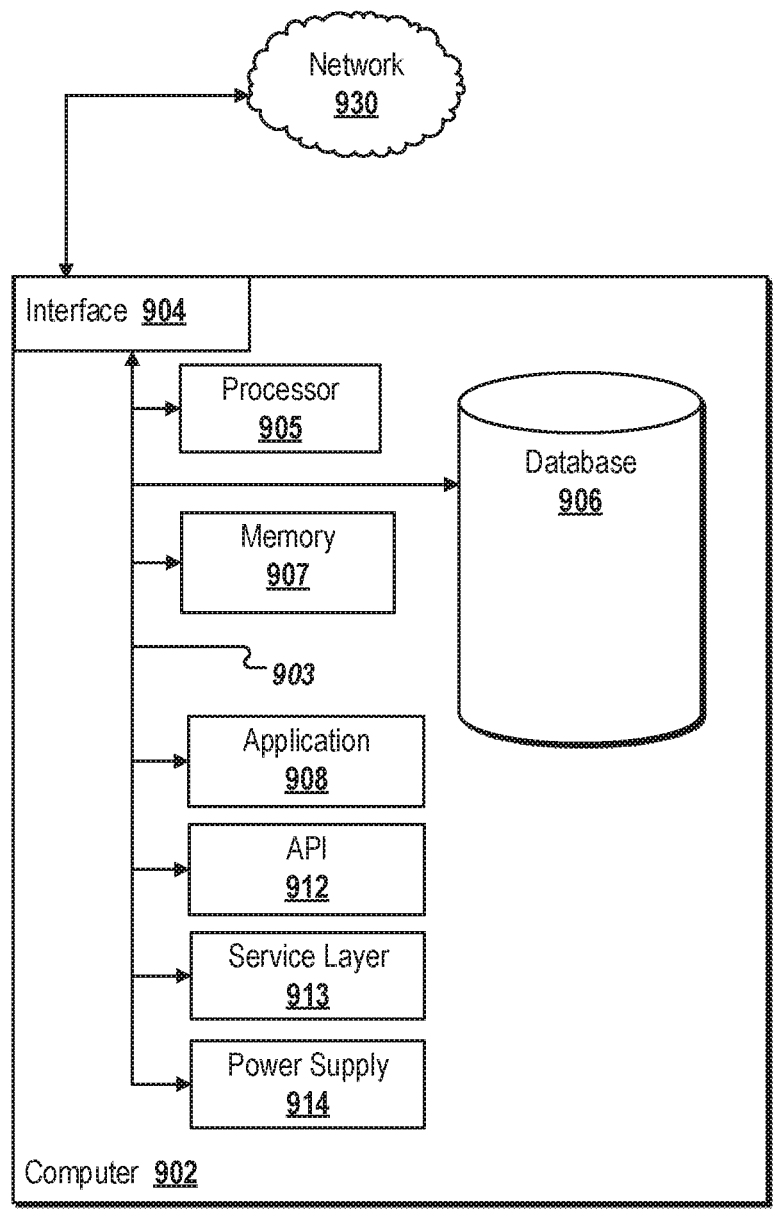
FIG. 9 is a block diagram illustrating an example of a computer-implemented system used to provide computational functionalities associated with described algorithms, methods, functions, processes, flows, and procedures, according to an implementation of the present disclosure.

FIG. 9 is a block diagram illustrating an example of a computer-implemented System 900 used to provide computational functionalities associated with described algorithms, methods, functions, processes, flows, and procedures, according to an implementation of the present disclosure. In the illustrated implementation, System 900 includes a Computer 902 and a Network 930.

The illustrated Computer 902 is intended to encompass any computing device such as a server, desktop computer, laptop/notebook computer, wireless data port, smart phone, personal data assistant (PDA), tablet computer, one or more processors within these devices, another computing device, or a combination of computing devices, including physical or virtual instances of the computing device, or a combination of physical or virtual instances of the computing device. Additionally, the Computer 902 can include an input device, such as a keypad, keyboard, touch screen, another input device, or a combination of input devices that can accept user information, and an output device that conveys information associated with the operation of the Computer 902, including digital data, visual, audio, another type of information, or a combination of types of information, on a graphical-type user interface (UI) (or GUI) or other UI.

The Computer 902 can serve in a role in a distributed computing system as a client, network component, a server, a database or another persistency, another role, or a combination of roles for performing the subject matter described in the present disclosure. The illustrated Computer 902 is communicably coupled with a Network 930. In some implementations, one or more components of the Computer 902 can be configured to operate within an environment, including cloud-computing-based, local, global, another environment, or a combination of environments.

At a high level, the Computer 902 is an electronic computing device operable to receive, transmit, process, store, or manage data and information associated with the described subject matter. According to some implementations, the Computer 902 can also include or be communicably coupled with a server, including an application server, e-mail server, web server, caching server, streaming data server, another server, or a combination of servers.

The Computer 902 can receive requests over Network 930 (for example, from a client software application executing on another Computer 902) and respond to the received requests by processing the received requests using a software application or a combination of software applications. In addition, requests can also be sent to the Computer 902 from internal users (for example, from a command console or by another internal access method), external or third-parties, or other entities, individuals, systems, or computers.

Each of the components of the Computer 902 can communicate using a System Bus 903. In some implementations, any or all of the components of the Computer 902, including hardware, software, or a combination of hardware and software, can interface over the System Bus 903 using an application programming interface (API) 912, a Service Layer 913, or a combination of the API 912 and Service Layer 913. The API 912 can include specifications for routines, data structures, and object classes. The API 912 can be either computer-language independent or dependent and refer to a complete interface, a single function, or even a set of APIs. The Service Layer 913 provides software services to the Computer 902 or other components (whether illustrated or not) that are communicably coupled to the Computer 902. The functionality of the Computer 902 can be accessible for all service consumers using the Service Layer 913. Software services, such as those provided by the Service Layer 913, provide reusable, defined functionalities through a defined interface. For example, the interface can be software written in JAVA, C++, another computing language, or a combination of computing languages providing data in extensible markup language (XML) format, another format, or a combination of formats. While illustrated as an integrated component of the Computer 902, alternative implementations can illustrate the API 912 or the Service Layer 913 as stand-alone components in relation to other components of the Computer 902 or other components (whether illustrated or not) that are communicably coupled to the Computer 902. Moreover, any or all parts of the API 912 or the Service Layer 913 can be implemented as a child or a sub-module of another software module, enterprise application, or hardware module without departing from the scope of the present disclosure.

The Computer 902 includes an Interface 904. Although illustrated as a single Interface 904, two or more Interfaces 904 can be used according to particular needs, desires, or particular implementations of the Computer 902. The Interface 904 is used by the Computer 902 for communicating with another computing system (whether illustrated or not) that is communicatively linked to the Network 930 in a distributed environment. Generally, the Interface 904 is operable to communicate with the Network 930 and includes logic encoded in software, hardware, or a combination of software and hardware. More specifically, the Interface 904 can include software supporting one or more communication protocols associated with communications such that the Network 930 or hardware of Interface 904 is operable to communicate physical signals within and outside of the illustrated Computer 902.

The Computer 902 includes a Processor 905. Although illustrated as a single Processor 905, two or more Processors 905 can be used according to particular needs, desires, or particular implementations of the Computer 902. Generally, the Processor 905 executes instructions and manipulates data to perform the operations of the Computer 902 and any algorithms, methods, functions, processes, flows, and procedures as described in the present disclosure.

The Computer 902 also includes a Database 906 that can hold data for the Computer 902, another component communicatively linked to the Network 930 (whether illustrated or not), or a combination of the Computer 902 and another component. For example, Database 906 can be an in-memory, conventional, or another type of database storing data consistent with the present disclosure. In some implementations, Database 906 can be a combination of two or more different database types (for example, a hybrid in-memory and conventional database) according to particular needs, desires, or particular implementations of the Computer 902 and the described functionality. Although illustrated as a single Database 906, two or more databases of similar or differing types can be used according to particular needs, desires, or particular implementations of the Computer 902 and the described functionality. While Database 906 is illustrated as an integral component of the Computer 902, in alternative implementations, Database 906 can be external to the Computer 902.

The Computer 902 also includes a Memory 907 that can hold data for the Computer 902, another component or components communicatively linked to the Network 930 (whether illustrated or not), or a combination of the Computer 902 and another component. Memory 907 can store any data consistent with the present disclosure. In some implementations, Memory 907 can be a combination of two or more different types of memory (for example, a combination of semiconductor and magnetic storage) according to particular needs, desires, or particular implementations of the Computer 902 and the described functionality. Although illustrated as a single Memory 907, two or more Memories 907 or similar or differing types can be used according to particular needs, desires, or particular implementations of the Computer 902 and the described functionality. While Memory 907 is illustrated as an integral component of the Computer 902, in alternative implementations, Memory 907 can be external to the Computer 902.

The Application 908 is an algorithmic software engine providing functionality according to particular needs, desires, or particular implementations of the Computer 902, particularly with respect to functionality described in the present disclosure. For example, Application 908 can serve as one or more components, modules, or applications. Further, although illustrated as a single Application 908, the Application 908 can be implemented as multiple Applications 908 on the Computer 902. In addition, although illustrated as integral to the Computer 902, in alternative implementations, the Application 908 can be external to the Computer 902.

The Computer 902 can also include a Power Supply 914. The Power Supply 914 can include a rechargeable or non-rechargeable battery that can be configured to be either user- or non-user-replaceable. In some implementations, the Power Supply 914 can include power-conversion or management circuits (including recharging, standby, or another power management functionality). In some implementations, the Power Supply 914 can include a power plug to allow the Computer 902 to be plugged into a wall socket or another power source to, for example, power the Computer 902 or recharge a rechargeable battery.

There can be any number of Computers 902 associated with, or external to, a computer system containing Computer 902, each Computer 902 communicating over Network 930. Further, the term "client," "user," or other appropriate terminology can be used interchangeably, as appropriate, without departing from the scope of the present disclosure. Moreover, the present disclosure contemplates that many users can use one Computer 902, or that one user can use multiple computers 902.

Described implementations of the subject matter can include one or more features, alone or in combination.

For example, in a first implementation, an apparatus, comprising: a first side plate and a second side plate; a spring configured to engage with the first side plate and the second side plate, the spring providing a spring bias to each of the first side plate and to the second side plate to bias a lower portion of the first side plate and a lower portion of the second side plate together into a default closed position; a medical extension device channel configured into each of the first side plate and the second side plate; and two anchor points configured as part of each of the first side plate and the second side plate.

The foregoing and other described implementations can each, optionally, include one or more of the following features:

A first feature, combinable with any of the following features, wherein the first side plate and the second side plate are each configured to define a spring tail engagement slot and a spring tail support shelf.

A second feature, combinable with any of the previous or following features, wherein the spring is configured to define two ninety-degree-angled spring tails, each spring tail configured to engage with the spring tail engagement slot and the spring tail support shelf.

A third feature, combinable with any of the previous or following features, wherein the first side plate and the second side plate are each configured with a plurality of pinch tabs to permit the lower portion of the first side plate and the lower portion of the second side plate to be separated when the pinch tabs are manipulated toward each other to overcome the spring bias of the spring.

A fourth feature, combinable with any of the previous or following features, wherein the medical extension device channel is configured with raised guidance elements to secure a medical extension device between the plurality of pinch tabs.

A fifth feature, combinable with any of the previous or following features, wherein the anchor points are configured to permit attachment of one or more securing bands to secure the medical extension device within the medical extension device channel.

A sixth feature, combinable with any of the previous or following features, further comprising a pivot cylinder and locking rivet to engage with two or more pivot arms configured as part of each of the first side plate and the second side plate, wherein the pivot cylinder, locking rivet, and two or more pivot arms are used to lock the first side plate and the second side plate together.

In a second implementation, an apparatus, comprising: a first side plate and a second side plate, wherein each of the first side plate and the second side plate comprises a male pivot point and a female pivot point to bear and rotate against each other; a spring configured to engage with the first side plate and the second side plate; a medical extension device channel configured into each of the first side plate and the second side plate; and two anchor points configured as part of each of the first side plate and the second side plate.

The foregoing and other described implementations can each, optionally, include one or more of the following features:

A first feature, combinable with any of the following features, wherein the male pivot point and the female pivot point of the first side plate are configured to engage with the female pivot point and the male pivot point of the second side plate, respectively.

A second feature, combinable with any of the previous or following features, wherein the spring provides a spring bias to each of the first side plate and to the second side plate to bias a lower portion of the first side plate and a lower portion of the second side plate together into a default closed position.

A third feature, combinable with any of the previous or following features, wherein the first side plate and the second side plate are each configured to define a spring tail engagement slot and a spring tail support shelf.

A fourth feature, combinable with any of the previous or following features, wherein the spring is configured to define two ninety-degree-angled spring tails, each spring tail configured to engage with the spring tail engagement slot and the spring tail support shelf of either the first side plate or the second side plate.

A fifth feature, combinable with any of the previous or following features, wherein the first side plate and the second side plate are each configured with a plurality of pinch tabs to permit a lower portion of the first side plate and a lower portion of the second side plate to be separated when the pinch tabs are manipulated toward each other to overcome a spring bias of the spring.

A sixth feature, combinable with any of the previous or following features, wherein the lower portion of the first side plate and the lower portion of the second side plate are separated when the pinch tabs are manipulated toward each other.

In a third implementation, a method, comprising: manipulating a plurality of pinch tabs together, wherein the plurality of pinch tabs are configured as part of each of a first side plate and a second side plate; and wherein the manipulation overcomes a spring bias of a spring to each of the first side plate and to the second side plate biasing a lower portion of the first side plate and a lower portion of the second side plate together into a default closed position; separating the lower portion of the first side plate and the lower portion of the second side plate; and allowing the manipulated plurality of pinch tabs to separate to grip a patient treatment platform at a position with the lower portion of the first side plate and the lower portion of the second side plate.

The foregoing and other described implementations can each, optionally, include one or more of the following features:

A first feature, combinable with any of the following features, further comprising receiving a medical extension device between the plurality of pinch tabs corresponding to either the first side plate or the second side plate.

A second feature, combinable with any of the previous or following features, further comprising securing, using a securing band, the received medical extension device against raised guidance elements configured as part of the first side plate and the second side plate.

A third feature, combinable with any of the previous or following features, further comprising manipulating the plurality of pinch tabs together to overcome the spring bias of the spring.

A fourth feature, combinable with any of the previous or following features, further comprising separating the lower portion of the first side plate and the lower portion of the second side plate.

A fifth feature, combinable with any of the previous or following features, further comprising allowing the manipulated pinch tabs to separate to grip the patient treatment platform at a different position with the lower portion of the first side plate and the lower portion of the second side plate.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable medium for execution by, or to control the operation of, a computer or computer-implemented system. Alternatively, or additionally, the program instructions can be encoded in/on an artificially generated propagated signal, for example, a machine-generated electrical, optical, or electromagnetic signal that is generated to encode information for transmission to a receiver apparatus for execution by a computer or computer-implemented system. The computer-storage medium can be a machine-readable storage device, a machine-readable storage substrate, a random or serial access memory device, or a combination of computer-storage mediums. Configuring one or more computers means that the one or more computers have installed hardware, firmware, or software (or combinations of hardware, firmware, and software) so that when the software is executed by the one or more computers, particular computing operations are performed.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second (s), or less than 5 s. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or an equivalent term as understood by one of ordinary skill in the art) refer to data processing hardware and encompass all kinds of apparatuses, devices, and machines for processing data, including by way of example, a programmable processor, a computer, or multiple processors or computers. The computer can also be, or further include special purpose logic circuitry, for example, a central processing unit (CPU), a field programmable gate array (FPGA), or an application-specific integrated circuit (ASIC). In some implementations, the computer or computer-implemented system or special purpose logic circuitry (or a combination of the computer or computer-implemented system and special purpose logic circuitry) can be hardware- or software-based (or a combination of both hardware- and software-based). The computer can optionally include code that creates an execution environment for computer programs, for example, code that constitutes processor firmware, a protocol stack, a database management system, an operating system, or a combination of execution environments. The present disclosure contemplates the use of a computer or computer-implemented system with an operating system of some type, for example LINUX, UNIX, WINDOWS, MAC OS, ANDROID, IOS, another operating system, or a combination of operating systems.

A computer program, which can also be referred to or described as a program, software, a software application, a unit, a module, a software module, a script, code, or other component can be written in any form of programming language, including compiled or interpreted languages, or declarative or procedural languages, and it can be deployed in any form, including, for example, as a stand-alone program, module, component, or subroutine, for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network.

While portions of the programs illustrated in the various figures can be illustrated as individual components, such as units or modules, that implement described features and functionality using various objects, methods, or other processes, the programs can instead include a number of sub-units, sub-modules, third-party services, components, libraries, and other components, as appropriate. Conversely, the features and functionality of various components can be combined into single components, as appropriate. Thresholds used to make computational determinations can be statically, dynamically, or both statically and dynamically determined.

Described methods, processes, or logic flows represent one or more examples of functionality consistent with the present disclosure and are not intended to limit the disclosure to the described or illustrated implementations, but to be accorded the widest scope consistent with described principles and features. The described methods, processes, or logic flows can be performed by one or more programmable computers executing one or more computer programs to perform functions by operating on input data and generating output data. The methods, processes, or logic flows can also be performed by, and computers can also be implemented as, special purpose logic circuitry, for example, a CPU, an FPGA, or an ASIC.

Computers for the execution of a computer program can be based on general or special purpose microprocessors, both, or another type of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable memory storage device.

Non-transitory computer-readable media for storing computer program instructions and data can include all forms of permanent/non-permanent or volatile/non-volatile memory, media and memory devices, including by way of example semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices; magnetic devices, for example, tape, cartridges, cassettes, internal/removable disks; magneto-optical disks; and optical memory devices, for example, digital versatile/video disc (DVD), compact disc (CD)-ROM, DVD+/−R, DVD-RAM, DVD-ROM, high-definition/density (HD)-DVD, and BLU-RAY/BLU-RAY DISC (BD), and other optical memory technologies. The memory can store various objects or data, including caches, classes, frameworks, applications, modules, backup data, jobs, web pages, web page templates, data structures, database tables, repositories storing dynamic information, or other appropriate information including any parameters, variables, algorithms, instructions, rules, constraints, or references. Additionally, the memory can include other appropriate data, such as logs, policies, security or access data, or reporting files. The processor and the memory can be supplemented by, or incorporated in, special purpose logic circuitry.

To provide for interaction with a user, implementations of the subject matter described in this specification can be implemented on a computer having a display device, for example, a cathode ray tube (CRT), liquid crystal display (LCD), light emitting diode (LED), or plasma monitor, for displaying information to the user and a keyboard and a pointing device, for example, a mouse, trackball, or trackpad by which the user can provide input to the computer. Input can also be provided to the computer using a touchscreen, such as a tablet computer surface with pressure sensitivity, a multi-touch screen using capacitive or electric sensing, or another type of touchscreen. Other types of devices can be used to interact with the user. For example, feedback provided to the user can be any form of sensory feedback (such as, visual, auditory, tactile, or a combination of feedback types). Input from the user can be received in any form, including acoustic, speech, or tactile input. In addition, a computer can interact with the user by sending documents to and receiving documents from a client computing device that is used by the user (for example, by sending web pages to a web browser on a user's mobile computing device in response to requests received from the web browser).

The term "graphical user interface," or "GUI," can be used in the singular or the plural to describe one or more graphical user interfaces and each of the displays of a particular graphical user interface. Therefore, a GUI can represent any graphical user interface, including but not limited to, a web browser, a touch screen, or a command line interface (CLI) that processes information and efficiently presents the information results to the user. In general, a GUI can include a number of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with the present disclosure), all or a portion of the Internet, another communication network, or a combination of communication networks. The communication network can communicate with, for example, Internet Protocol (IP) packets, frame relay frames, Asynchronous Transfer Mode (ATM) cells, voice, video, data, or other information between network nodes.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any inventive concept or on the scope of what can be claimed, but rather as descriptions of features that can be specific to particular implementations of particular inventive concepts. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features can be described as acting in certain combinations and even initially claimed as such, one or more features from a claimed combination can, in some cases, be excised from the combination, and the claimed combination can be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations can be considered optional), to achieve desirable results. In certain circumstances, multitasking or parallel processing (or a combination of multitasking and parallel processing) can be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

The invention claimed is:

1. An apparatus, comprising:
   a first side plate and a second side plate;
   a spring configured to engage with the first side plate and the second side plate, the spring providing a spring bias to each of the first side plate and to the second side plate to bias a lower portion of the first side plate and a lower portion of the second side plate together into a default closed position;
   a medical extension device channel configured into each of the first side plate and the second side plate; and
   two anchor points configured as part of each of the first side plate and the second side plate, wherein the anchor points are configured to permit attachment of one or more securing bands to secure a medical extension device within the medical extension device channel.

2. The apparatus of claim 1, wherein the first side plate and the second side plate are each configured to define a spring tail engagement slot and a spring tail support shelf.

3. The apparatus of claim 2, wherein the spring is configured to define two ninety-degree-angled spring tails, each spring tail configured to engage with the spring tail engagement slot and the spring tail support shelf.

4. The apparatus of claim 1, wherein the first side plate and the second side plate are each configured with a plurality of pinch tabs to permit the lower portion of the first side plate and the lower portion of the second side plate to be separated when the pinch tabs are manipulated toward each other to overcome the spring bias of the spring.

5. The apparatus of claim 4, wherein the medical extension device channel is configured with raised guidance elements to secure the medical extension device between the plurality of pinch tabs.

6. The apparatus of claim 1, further comprising a pivot cylinder and locking rivet to engage with two or more pivot arms configured as part of each of the first side plate and the second side plate, wherein the pivot cylinder, locking rivet, and two or more pivot arms are used to lock the first side plate and the second side plate together.

7. An apparatus, comprising:
   a first side plate and a second side plate, wherein each of the first side plate and the second side plate comprises a male pivot point and a female pivot point to bear and rotate against each other;
   a spring configured to engage with the first side plate and the second side plate;
   a medical extension device channel configured into each of the first side plate and the second side plate; and
   two anchor points configured as part of each of the first side plate and the second side plate, wherein the anchor points are configured to permit attachment of one or more securing bands to secure a medical extension device within the medical extension device channel.

8. The apparatus of claim 7, wherein the male pivot point and the female pivot point of the first side plate are configured to engage with the female pivot point and the male pivot point of the second side plate, respectively.

9. The apparatus of claim 7, wherein the spring provides a spring bias to each of the first side plate and to the second side plate to bias a lower portion of the first side plate and a lower portion of the second side plate together into a default closed position.

10. The apparatus of claim 7, wherein the first side plate and the second side plate are each configured to define a spring tail engagement slot and a spring tail support shelf.

11. The apparatus of claim 10, wherein the spring is configured to define two ninety-degree-angled spring tails, each spring tail configured to engage with the spring tail engagement slot and the spring tail support shelf of either the first side plate or the second side plate.

12. The apparatus of claim 7, wherein the first side plate and the second side plate are each configured with a plurality of pinch tabs to permit a lower portion of the first side plate and a lower portion of the second side plate to be separated when the pinch tabs are manipulated toward each other to overcome a spring bias of the spring.

13. The apparatus of claim 12, wherein the lower portion of the first side plate and the lower portion of the second side plate are separated when the pinch tabs are manipulated toward each other.

14. A method, comprising:
  manipulating a plurality of pinch tabs together, wherein the plurality of pinch tabs are configured as part of each of a first side plate and a second side plate; and wherein the manipulation overcomes a spring bias of a spring to each of the first side plate and to the second side plate biasing a lower portion of the first side plate and a lower portion of the second side plate together into a default closed position;
  separating the lower portion of the first side plate and the lower portion of the second side plate;
  allowing the manipulated plurality of pinch tabs to separate to grip a patient treatment platform at a position with the lower portion of the first side plate and the lower portion of the second side plate; and
  securing, using anchor points configured as part of either the first side plate or the second side plate and a securing band, a received medical extension device against raised guidance elements configured as part of either the first side plate or the second side plate.

15. The method of claim 14, further comprising receiving the medical extension device between the plurality of pinch tabs corresponding to either the first side plate or the second side plate.

16. The method of claim 14, further comprising manipulating the plurality of pinch tabs together to overcome the spring bias of the spring.

17. The method of claim 16, further comprising separating the lower portion of the first side plate and the lower portion of the second side plate.

18. The method of claim 17, further comprising allowing the manipulated pinch tabs to separate to grip the patient treatment platform at a different position with the lower portion of the first side plate and the lower portion of the second side plate.

* * * * *